United States Patent [19]

Stebles

[11] 4,134,968
[45] Jan. 16, 1979

[54] SINGLE PHASE WATER CONTAINING AEROSOL COMPOSITIONS

[75] Inventor: Malcolm R. D. Stebles, Maidenhead, England

[73] Assignee: Lever Brothers Company, New York, N.Y.

[21] Appl. No.: 767,605

[22] Filed: Feb. 10, 1977

[30] Foreign Application Priority Data

Feb. 18, 1976 [GB] United Kingdom ................. 6410/76

[51] Int. Cl.² ................................................ A61K 7/11
[52] U.S. Cl. ..................................... 424/47; 8/127.51;
252/305; 252/522; 424/DIG. 1; 424/45;
424/65; 424/68; 424/71
[58] Field of Search ................. 8/127.51; 424/DIG. 1,
424/DIG. 2, 45, 47, 71, 68, 65; 252/305, 522

[56] References Cited

U.S. PATENT DOCUMENTS

| | | | |
|---|---|---|---|
| 3,479,427 | 11/1969 | Lieberman et al. | 424/47 |
| 3,790,664 | 2/1974 | Krochock et al. | 424/47 |
| 3,981,987 | 9/1976 | Linke et al. | 424/47 |

*Primary Examiner*—Albert T. Meyers
*Assistant Examiner*—Vera C. Clarke
*Attorney, Agent, or Firm*—James J. Farrell; Melvin H. Kurtz; Kenneth F. Dusyn

[57] ABSTRACT

An aerosol composition comprising a liquid mixture of hydrocarbon propellant, an alcoholic solvent and, to reduce flammability, water and methylene chloride and/or 1,1,1-trichloroethane, wherein the liquid mixture forms a single phase consisting essentially of 5–30% by weight of the hydrocarbon propellant, 5–30% by weight of water, 10–40% by weight of methylene chloride and/or 1,1,1-trichloroethane, and 37–80% by weight of ethanol, n-propanol or isopropanol. The composition does not require to be shaken before use.

6 Claims, No Drawings

SINGLE PHASE WATER CONTAINING AEROSOL COMPOSITIONS

This invention relates to aerosol compositions.

Aerosol compositions are known which comprise an alcoholic or aqueous alcoholic solution of an active ingredient, for example a hairspray resin, and a propellant consisting of a fluorinated hydrocarbon gas or mixture of fluorohydrocarbon gases liquefied under pressure.

An alternative to the use of fluorohydrocarbon propellants is the use of liquefied hydrocarbons, particularly propane and the butanes. While it is known that the flammability of aerosol sprays which utilise hydrocarbon propellants can be reduced by including in the composition methylene chloride or 1,1,1-trichloroethane, or a mixture of them, it is conventional practice in the art to include water in hydrocarbon-based aerosol compositions to reduce flammability. There are, in fact, a number of water-containing hydrocarbon-based aerosol products commercially available at the present time and these products are two-phase systems. These products, however, have the disadvantages associated with two-phase systems, that is they have to be shaken before use and often a spray valve utilising a vapour phase tap is required to be used to prevent liquid hydrocarbon being left in the container and/or to improve the break-up of the water-containing spray.

We have now discovered certain compositions which although containing a sufficient amount of hydrocarbon propellant to produce adequate break-up of the sprayed composition throughout the life of an aerosol container, and although also containing both water and methylene chloride and/or 1,1,1-trichloroethane to reduce the flammability of the composition when sprayed, are nevertheless single phase compositions thereby overcoming the aforementioned disadvantages of two-phase systems.

According to the invention there is provided an aerosol composition within an aerosol container comprising a liquid mixture of a hydrocarbon propellant, water and an organic solvent, wherein the liquid mixture forms a single phase and consists essentially of:

(a) 5 to 30%, preferably 10 to 20%, by weight of a hydrocarbon propellant to give a pressure within the aerosol container of 1.5 to 8.5 kg/cm$^2$ at 25° C.;

(b) 5 to 30%, preferably 5 to 20%, by weight of water;

(c) 10 to 40%, preferably 15 to 30%, by weight of methylene chloride or 1,1,1-trichloroethane or a mixture thereof; and (d) at least 37%, preferably 37 to 70%, by weight of ethanol, n-propanol or iso-propanol.

By the reference above to the single phase liquid mixture consisting essentially of ingredients (a) to (d) it is meant that at least 95% by weight of the liquid mixture is made up of these specified constituents. However, minor amounts of other organic liquids may be included provided that they do not adversely affect significantly the properties of the composition; examples are dimethoxymethane, ethyl acetate, acetone, dimethylether, diethylether, 2-methoxyethanol, 2-ethoxyethanol or a butanol.

The hydrocarbon propellant may be, for example, propane, iso-butane, n-butane or blends of these materials. Commercially available blends may contain small proportions of higher saturated hydrocarbons. Other hydrocarbon components, such as hexane, may be blended with propane or butanes to produce pressures within the stated range. Particularly suitable hydrocarbon propellants are the commercially available Calor Aerosol Propellants which have vapour pressures ranging from about 2.5 to about 8.5 bars at 25° C. Optionally, compressed gases such as carbon dioxide and/or nitrous oxide can be included in the aerosol composition.

An active ingredient may be included in the aerosol composition of the invention, for example a hair conditioning agent, hairspray resin, antiperspirant agent, bactericide, perfume or odour-suppressing material. Suitable mixtures may also be used.

As a hairspray resin one may employ any resin usually used for this purpose and in particular the resins obtained from film-forming polymers, such as polyvinylpyrrolidone, polyvinylpyrrolidone/vinyl acetate copolymers: copolymers of vinyl acetate and an unsaturated carboxylic acid such as crotonic acid; copolymers resulting from the copolymerisation of vinyl acetate, crotonic acid and an acrylic or methacrylic ester; copolymers resulting from the copolymerisation of vinyl acetate, crotonic acid and a vinyl ester of an acid with a long carbon chain, or an allyl or methallyl ester of an acid with a long carbon chain; copolymers resulting from the copolymerisation of vinyl acetate and a vinyl alkyl ether; copolymers resulting from the copolymerisation of a vinyl alkyl ether and maleic anhydride, which copolymers are partly or completely esterified with a saturated aliphatic alcohol; copolymers resulting from the copolymerisation of an ester derived from an unsaturated alcohol and an acid with a short carbon chain, and unsaturated acid with a short chain, and at least one ester derived from a saturated alcohol with a short chain and an unsaturated acid; and copolymers resulting from the copolymerisation of at least one unsaturated ester and at least one unsaturated acid.

The copolymers which possess acid groups can optionally be neutralised by means of an organic or inorganic base so as to increase their solubility in order to facilitate their use.

By way of example, bases such as monoethanolamine, diethanolamine, triethanolamine, the isopropanolamines, morpholine, 2-amino-2-methyl-1-propanol, or 2-amino-2-methyl-1,3-propanediol can be used for this purpose.

The hairspray may be modified by the addition of other active ingredients such as plasticisers, for example diethylene glycol, polethylene glycol, hexylene glycol, diethyl adipate, dimethyl phthalate, diethyl phthalate or dibutyl phthalate, and polydimethylsiloxane-polyoxyalkylene block copolymers as described in U.S. Pat. No. 3,928,558.

Hairspray resins are usually employed in aerosol compositions in amounts of from about 0.1 to 7.5% by weight of the composition.

Suitable antiperspirant agents which may be employed in the aerosol compositions of the invention are the well known aluminium and zirconium astringent materials, for example aluminium chlorhydroxide.

Other minor ingredients, such as denaturants and anticorrosive agents, may also be included in the aerosol compositions of the invention.

The following Examples of aerosol compositions illustrate the invention. In each case the ingredients were filled into a 6 oz (170 g) container. Percentages are by weight. All pressures are given at 25° C.

EXAMPLE 1

An aerosol hairspray was made having the following composition:

| Ingredient | g |
| --- | --- |
| Hairspray resin (National Starch Resyn 28-2930) | 2.000 |
| 2-Amino-2-methyl-1-propanol | 0.186 |
| Methylene chloride | 25.000 |
| Water | 10.000 |
| Hydrocarbon propellant (CAP 40) | 18.000 |
| Industrial methylated spirit (74 OP) | to 100.000 |

The resin employed was a polymer of vinyl acetate (75%), crotonic acid (10%) and vinyl versatate (15%).

The hydrocarbon propellant was Calor Aerosol Propellant Grade 40, a commercial hydrocarbon blend consisting mainly of a mixture of propane and butanes having a vapour pressure of about 3.2 bars.

The composition was made by dissolving the aminomethyl propanol in the industrial methylated spirit to which the resin was then added. To this solution was added the methylene chloride and water and the mixture put in an aerosol container. A valve was vacuum crimped on the container which was then filled with the propellant through the valve. The pressure in the aerosol container was 2.53 kg/cm$^2$.

The aerosol composition consisted of a solution of the neutralised resin in the single liquid phase formed by the other constituents and consequently did not require to be shaken before use. The amount of propellant was sufficient to discharge all the contents of the container.

EXAMPLE 2

The aerosol hairspray was made having the following composition:

| Ingredient | g |
| --- | --- |
| Hairspray resin (Luviskol 37I) | 4.0 |
| Methylene chloride | 25.0 |
| Water | 11.0 |
| Hydrocarbon propellant (as in Example 1) | 17.0 |
| Iso-propanol | 43.0 |

The hairspray resin employed in this example (Luviskol 37I) was a 50% solution in iso-propanol of a copolymer of vinyl acetate (70%) and vinyl pyrrolidone (30%).

The composition was made by adding the Luviskol 37I to the iso-propanol followed by the addition of the methylene chloride and water. The procedure was then as in Examples 1. The pressure in the aerosol container was 2.32 kg/cm$^2$.

By reason of the fact that the composition consisted of a single phase the container did not need to be shaken before use. The amount of the propellant was sufficient to discharge the whole of the contents of the can.

EXAMPLE 3

An aerosol hairspray was made having the following composition:

| Ingredient | g |
| --- | --- |
| Hairspray resin (as in Example 1) | 1.00 |
| 2-Amino-2-methyl-1-propanol | 0.09 |
| Methylene chloride | 25.00 |
| Water | 10.00 |
| Hydrocarbon propellant (as in Example 1) | 10.00 |
| Carbon dioxide | 2.00 |
| Ethanol | to 100.00 |

The composition was made by dissolving the aminomethyl propanol in the ethanol to which the resin was then added. To this solution was added the methylene chloride and water and the mixture put in an aerosol container. A valve was crimped on the container and the hydrocarbon propellant and carbon dioxide introduced into the container through the valve. The pressure in the aerosol container was 4.92 kg/cm$^2$. The aerosol composition consisted of a solution of the neutralised resin in the single liquid phase formed by the mixture of liquid constituents and did not require to be shaken before use. The amount of propellant was sufficient to discharge all the contents of the container.

EXAMPLE 4

An aerosol hairspray was made having the following composition:

| Ingredient | g |
| --- | --- |
| Hairspray resin (as in Example 1) | 1.00 |
| 2-Amino-2-methyl-1-propanol | 0.09 |
| Methylene chloride | 25.00 |
| Water | 10.00 |
| CAP 40 | 12.00 |
| n-Hexane | 6.00 |
| 2-Methoxyethanol | 4.50 |
| Ethanol | to 100.00 |

The composition was made by dissolving the aminomethyl propanol in the ethanol to which the resin was then added. To this solution was added the methylene chloride, water, methoxyethanol and hexane and the mixture was then filled into an aerosol container. A valve was crimped on the container and the CAP 40 introduced through the valve. The pressure in the aerosol container was 3.09 kg/cm$^2$. The aerosol composition consisted of a solution of the neutralised resin in the single liquid phase formed by the other ingredients and did not require to be shaken before use. The amount of propellant was sufficient to discharge all the contents of the container.

EXAMPLE 5

An aerosol hair setting aid was made having the following composition:

| Ingredient | g |
| --- | --- |
| Hair setting resin | 2.0 |
| Methylene chloride | 10.0 |
| Water | 19.0 |
| Hydrocarbon propellant (as in Example 1) | 7.0 |
| Ethanol | 62.0 |

The hair setting resin was a copolymer of vinyl pyrrolidone (60%) and vinyl acetate (40%).

The composition was made by dissolving the resin in the ethanol of which was then added the methylene chloride and water. The mixture was put into an aerosol container and a valve crimped on. The hydrocarbon propellant was then introduced through the valve. The pressure in the aerosol container was 2.80 kg/cm². The aerosol composition consisted of a solution of the hair setting resin in the single liquid phase formed by the other constituents and consequently did not require to be shaken before use. The amount of propellant was sufficient to discharge all the contents of the container.

EXAMPLE 6

An aerosol space spray was made having the following composition:

| Ingredient | g |
| --- | --- |
| Perfume | 0.5 |
| Methylene chloride | 10.0 |
| Water | 15.0 |
| Hydrocarbon propellant (as in Example 1) | 17.0 |
| Industrial methylated spirit | to 100.0 |

The composition was made by dissolving the perfume in the industrial methylated spirit to which was then added the methylene chloride and water. The mixture was put in an aerosol container and a valve vacuum crimped on. The hydrocarbon propellant was then introduced through the valve. The pressure in the aerosol container was 3.59 kg/cm².

The aerosol composition consisted of a solution of the perfume in the single liquid phase formed by the other ingredients and did not require to be shaken before use. The amount of propellant was sufficient to discharge all the contents of the container.

EXAMPLE 7

An aerosol space spray was made having the following composition:

| Ingredient | g |
| --- | --- |
| Hydrocarbon propellant (as in Example 1) | 15.0 |
| Water | 8.0 |
| Methylene chloride | 10.0 |
| Perfume | 0.5 |
| Ethanol | 66.5 |

The composition was made by dissolving the perfume in the ethanol of which was then added the methylene chloride and water. The mixture was put in an aerosol container and a valve crimped on. The hydrocarbon propellant was then introduced through the valve. The pressure in the aerosol container was 2.25 kg/cm².

The aerosol composition consisted of a solution of the perfume in the single liquid phase formed by the other ingredients and did not require to be shaken before use. The amount of propellant was sufficient to discharge all the contents of the container.

EXAMPLE 8

An aerosol deodorant was made having the following composition:

| Ingredient | g |
| --- | --- |
| 2,4,4'-Trichloro-2'-hydroxy-diphenyl ether (Irgasan DP300) | 0.2 |
| Methylene chloride | 25.0 |
| Water | 10.0 |
| Hydrocarbon propellant (as in Example 1) | 18.0 |
| Industrial methylated spirit | to 100.0 |

The composition was made by dissolving the bactericide in the industrial methylated spirit to which was added the methylene chloride and the water. The mixture was placed in an aerosol container and a valve vacuum crimped on the container which was then filled with the hydrocarbon propellant through the valve. The pressure in the aerosol container was 3.23 kg/cm².

The aerosol composition consisted of a solution of the bactericide in the single liquid phase formed by the other constituents and did not require to be shaken before use. The amount of propellant was sufficient to discharge all the contents of the container.

EXAMPLE 9

An aerosol deodorant was made having the following composition:

| Ingredient | g |
| --- | --- |
| 2,4,4'-Trichloro-2'-hydroxy-diphenyl ether (Irgasan DP300) | 0.2 |
| Methylene chloride | 25.0 |
| 1,1,1-Trichloroethane | 5.0 |
| Water | 5.0 |
| Hydrocarbon propellant (as in Example 1) | 25.0 |
| Ethanol | to 100.0 |

The composition was made by dissolving the bactericide in the ethanol to which was added the methylene chloride, trichloroethane and the water. The mixture was then placed in an aerosol container and a valve crimped on the container which was then filled with the hydrocarbon propellant through the valve. The pressure in the aerosol container was 2.95 kg/cm².

The aerosol composition consisted of a solution of the bactericide in the single liquid phase formed by the other constituents and did not require to be shaken before use. The amount of propellant was sufficient to discharge all the contents of the container.

EXAMPLE 10

An aerosol antiperspirant was made having the following composition:

| Ingredient | g |
| --- | --- |
| Aluminium chlorhydroxide-propylene glycol complex (Rehydrol) | 10.0 |
| Methylene chloride | 10.0 |
| Water | 10.0 |
| Hydrocarbon propellant (as in Example 1) | 15.0 |
| Industrial methylated spirit | to 100.0 |

The composition was made by dissolving the antiperspirant active agent in the industrial methylated spirit and water to which was then added the methylene chloride. The mixture was then put in an aerosol container and a valve crimped on. The hydrocarbon propellant was introduced through the valve. The pressure in the aerosol container was 2.60 kg/cm².

The composition consisted of a solution of the aluminium chlorhydroxide-propylene glycol complex in the single liquid phase formed by the other constituents of the composition and did not require to be shaken before use. The amount of propellant was sufficient to discharge all the contents of the container.

What is claimed is:

1. An aerosol composition within an aerosol container comprising a liquid mixture of a hydrocarbon propellant, water and an organic solvent, wherein the liquid mixture forms a single phase and consists essentially of:
  (a) about 5 to about 30% by weight of a hydrocarbon propellant to give a pressure within the aerosol container of 1.5 to 8.5 kg/cm$^2$ at 25° C.;
  (b) about 5 to about 30% by weight of water;
  (c) about 10 to about 40% by weight of a chlorinated solvent selected from the group consisting of methylene chloride and 1,1,1-trichloroethane; and
  (d) about 37 to about 80% by weight of an alcohol selected from the group consisting of ethanol, n-propanol and iso-propanol.

2. A composition as claimed in claim 1 comprising about 10 to about 20% by weight of the hydrocarbon propellant.

3. A composition as claimed in claim 1 comprising about 5 to about 20% by weight of water.

4. A composition as claimed in claim 1 comprising about 15 to about 30% by weight of the chlorinated solvent.

5. A composition as claimed in claim 1, wherein the hydrocarbon propellant is selected from the group consisting of propane, iso-butane, n-butane and mixtures thereof.

6. A composition as claimed in claim 1 comprising additionally about 0.1 to about 7.5% by weight of a hairspray resin.

* * * * *